(12) United States Patent
Morrissey

(10) Patent No.: US 10,751,177 B2
(45) Date of Patent: Aug. 25, 2020

(54) FLEXIBLE CATHETER AND METHODS OF FORMING SAME

(71) Applicant: St. Jude Medical, Cardiology Division, Inc., St. Paul, MN (US)

(72) Inventor: Michael Shane Morrissey, St. Paul, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 868 days.

(21) Appl. No.: 14/881,330

(22) Filed: Oct. 13, 2015

(65) Prior Publication Data

US 2016/0100942 A1    Apr. 14, 2016

Related U.S. Application Data

(60) Provisional application No. 62/063,553, filed on Oct. 14, 2014.

(51) Int. Cl.
*A61F 2/24* (2006.01)
*A61M 25/01* (2006.01)
(Continued)

(52) U.S. Cl.
CPC .......... *A61F 2/2436* (2013.01); *A61B 1/0055* (2013.01); *A61B 2017/00314* (2013.01); *A61F 2/97* (2013.01); *A61F 2220/0083* (2013.01); *A61F 2220/0091* (2013.01); *A61F 2240/001* (2013.01); *A61M 25/0138* (2013.01)

(58) Field of Classification Search
CPC ............. A61F 2/2436; A61M 25/0138; A61M 25/141; A61M 25/0054; A61M 25/0147; A61B 1/0056; A61B 1/0051
See application file for complete search history.

(56) References Cited

U.S. PATENT DOCUMENTS

| 3,657,744 A | 4/1972 | Ersek |
| 4,423,730 A | 1/1984 | Gabbay |

(Continued)

FOREIGN PATENT DOCUMENTS

| EP | 1129744 A1 | 9/2001 |
| EP | 1157673 A2 | 11/2001 |

(Continued)

OTHER PUBLICATIONS

International Search Report and Written Opinion for Application No. PCT/IB2013/000903 dated Aug. 2, 2013.
(Continued)

*Primary Examiner* — Alexander J Orkin
(74) *Attorney, Agent, or Firm* — Lerner, David, Littenberg, Krumholz & Mentlik, LLP

(57) ABSTRACT

A delivery device for a collapsible prosthetic heart valve includes an outer shaft having a first end and a second end, an inner shaft disposed inside the outer shaft and longitudinally movable relative to the outer shaft, and a distal sheath coupled to the inner shaft and movable with the inner shaft to selectively cover and uncover a compartment for housing the valve. The outer shaft includes a plurality of disks each having at least two hinges to allow articulation of adjacent disks relative to one another, and at least one rib for coupling the adjacent disks to one another.

13 Claims, 9 Drawing Sheets

(51) Int. Cl.
  *A61B 17/00* (2006.01)
  *A61F 2/97* (2013.01)
  *A61B 1/005* (2006.01)

(56) References Cited

U.S. PATENT DOCUMENTS

| | | | |
|---|---|---|---|
| 5,749,828 A * | 5/1998 | Solomon | A61B 1/0055 600/139 |
| 5,807,241 A * | 9/1998 | Heimberger | A61B 1/0055 600/139 |
| 5,843,167 A | 12/1998 | Dwyer et al. | |
| 5,879,352 A * | 3/1999 | Filoso | A61B 17/7013 606/60 |
| 5,924,424 A | 7/1999 | Stevens et al. | |
| 5,968,068 A | 10/1999 | Dehdashtian et al. | |
| 6,077,297 A | 6/2000 | Robinson et al. | |
| 6,299,637 B1 * | 10/2001 | Shaolian | A61F 2/2418 623/1.24 |
| 6,306,141 B1 | 10/2001 | Jervis | |
| 6,364,828 B1 * | 4/2002 | Yeung | A61B 1/0056 174/68.3 |
| 6,623,518 B2 | 9/2003 | Thompson et al. | |
| 6,814,746 B2 | 11/2004 | Thompson et al. | |
| 6,830,584 B1 | 12/2004 | Seguin | |
| 7,018,406 B2 | 3/2006 | Seguin et al. | |
| 7,311,730 B2 | 12/2007 | Gabbay | |
| 7,510,572 B2 | 3/2009 | Gabbay | |
| 7,682,390 B2 | 3/2010 | Seguin | |
| 7,803,185 B2 | 9/2010 | Gabbay | |
| 8,287,541 B2 * | 10/2012 | Nelson | A61B 17/1717 606/62 |
| 2003/0050694 A1 | 3/2003 | Yang et al. | |
| 2004/0210304 A1 | 10/2004 | Seguin et al. | |
| 2005/0137695 A1 | 6/2005 | Salahieh et al. | |
| 2005/0137697 A1 | 6/2005 | Salahieh et al. | |
| 2005/0273085 A1 * | 12/2005 | Hinman | A61B 1/0055 606/1 |
| 2006/0074484 A1 | 4/2006 | Huber | |
| 2006/0106415 A1 | 5/2006 | Gabbay | |
| 2006/0142848 A1 | 6/2006 | Gabbay | |
| 2006/0167468 A1 | 7/2006 | Gabbay | |
| 2006/0259120 A1 | 11/2006 | Vongphakdy et al. | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0073391 A1 | 3/2007 | Bourang et al. | |
| 2007/0088431 A1 | 4/2007 | Bourang et al. | |
| 2007/0112422 A1 | 5/2007 | Dehdashtian | |
| 2007/0162100 A1 | 7/2007 | Gabbay | |
| 2007/0168013 A1 | 7/2007 | Douglas | |
| 2007/0203575 A1 | 8/2007 | Forster et al. | |
| 2007/0239271 A1 | 10/2007 | Nguyen | |
| 2007/0244552 A1 | 10/2007 | Salahieh et al. | |
| 2008/0071369 A1 | 3/2008 | Tuval et al. | |
| 2008/0097298 A1 * | 4/2008 | Fisher | A61B 17/320758 604/103.04 |
| 2008/0147182 A1 | 6/2008 | Righini et al. | |
| 2008/0188928 A1 * | 8/2008 | Salahieh | A61M 25/0054 623/2.11 |
| 2008/0249364 A1 * | 10/2008 | Korner | A61B 1/00071 600/141 |
| 2009/0054975 A1 | 2/2009 | del Nido et al. | |
| 2009/0062602 A1 | 3/2009 | Rosenberg et al. | |
| 2009/0099554 A1 | 4/2009 | Forster et al. | |
| 2009/0234443 A1 * | 9/2009 | Ottma | A61F 2/2436 623/2.11 |
| 2010/0004740 A1 | 1/2010 | Seguin et al. | |
| 2010/0049313 A1 | 2/2010 | Alon et al. | |
| 2010/0286626 A1 | 11/2010 | Petersen et al. | |
| 2010/0286768 A1 | 11/2010 | Alkhatib | |
| 2010/0298931 A1 | 11/2010 | Quadri et al. | |
| 2011/0224678 A1 | 9/2011 | Gabbay | |
| 2012/0277730 A1 * | 11/2012 | Salahieh | A61B 1/00135 604/527 |
| 2013/0166020 A1 * | 6/2013 | Hillukka | A61F 2/2427 623/2.11 |
| 2013/0226151 A1 * | 8/2013 | Suehara | A61M 39/1055 604/533 |
| 2013/0296718 A1 | 11/2013 | Ranganathan et al. | |
| 2014/0005718 A1 * | 1/2014 | Shelton, IV | A61B 17/07207 606/205 |
| 2014/0214153 A1 | 7/2014 | Ottma et al. | |

FOREIGN PATENT DOCUMENTS

| | | |
|---|---|---|
| EP | 1926455 A2 | 6/2008 |
| WO | 2004011076 A2 | 2/2004 |
| WO | 07071436 A2 | 6/2007 |
| WO | 08070797 A2 | 6/2008 |
| WO | 2009091509 A1 | 7/2009 |
| WO | 2009112060 A1 | 9/2009 |
| WO | 10051025 A1 | 5/2010 |
| WO | 10087975 A1 | 8/2010 |
| WO | 2011041720 A2 | 4/2011 |

OTHER PUBLICATIONS

Ruiz, Carlos, Overview of PRE-CE Mark Transcatheter Aortic Valve Technologies, Euro PCR May 25, 2010.

Percutaneous aortic valve replacement: resection before implantation, 836-840, Quaden, Rene et al., European J. of Cardio-thoracic Surgery, 27 (2005).

* cited by examiner

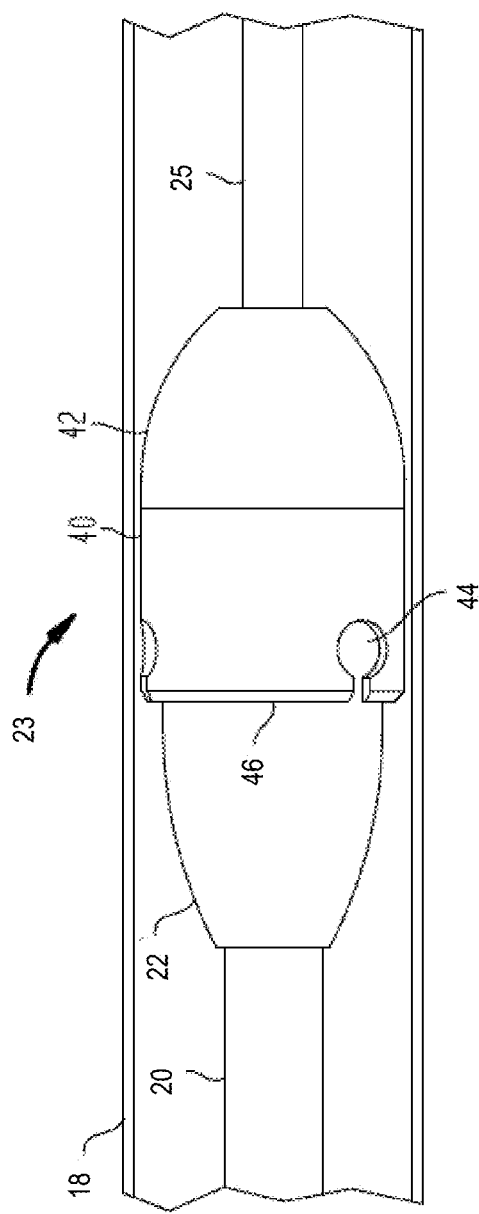

FLEXIBLE CATHETER AND METHODS OF FORMING SAME

CROSS-REFERENCE TO RELATED APPLICATIONS

The present application claims the benefit of the filing date of U.S. Provisional Patent Application No. 62/063,553 filed Oct. 14, 2014, the disclosure of which is hereby incorporated herein by reference.

BACKGROUND OF THE INVENTION

The present disclosure relates to delivery devices for implanting medical devices such as prosthetic heart valves and, more particularly, to assemblies and methods for forming delivery devices having greater flexibility.

Prosthetic heart valves may be formed from biological materials such as harvested bovine valves or pericardial tissue. Such valves are typically fitted within a stent, which may be inserted into the heart at the annulus of the compromised native valve to replace the native valve. To perform such an insertion procedure using a minimally invasive technique, it is typically necessary to compress the stent to a reduced diameter for loading into the delivery device.

Once loaded, the delivery device having the prosthetic heart valve is advanced through the patient's body until it reaches the implantation site. Due to the size of the arteries and the tortuosity of the delivery route, it may be difficult to maneuver the delivery system to the implantation site. It would therefore be beneficial to provide a delivery device having a greater degree of flexibility that can more readily navigate tortuous paths.

BRIEF SUMMARY OF THE DISCLOSURE

In some embodiments, a delivery device for a collapsible prosthetic heart valve includes an outer shaft having a first end and a second end, an inner shaft disposed inside the outer shaft and longitudinally movable relative to the outer shaft, and a distal sheath coupled to the inner shaft and movable with the inner shaft to selectively cover and uncover a compartment for housing the valve. The outer shaft includes a plurality of disks each having at least one hinge to allow articulation of adjacent disks relative to one another, and at least one rib for coupling the adjacent disks to one another.

In some embodiments, a catheter includes an elongated tubular body having a first end and a second end and including a plurality of disks each having at least two hinges to allow articulation of adjacent disks relative to one another, and at least one rib for coupling the adjacent disks to one another.

In some embodiments, a method of forming a delivery device for a collapsible prosthetic heart valve includes providing an outer shaft having a first end and a second end, an inner shaft disposed inside the outer shaft and longitudinally movable relative to the outer shaft, and a distal sheath coupled to the inner shaft and movable with the inner shaft to selectively cover and uncover a compartment for housing the valve. A series of circumferential patterns may be cut on the outer shaft at different axial lengths to form a plurality of disks each having at least two hinges to allow articulation of adjacent disks relative to one another, and at least one rib for coupling the adjacent disks to one another.

BRIEF DESCRIPTION OF THE DRAWINGS

Various embodiments of the present delivery device are disclosed herein with reference to the drawings, wherein:

FIG. 3 is an enlarged side view of a retaining element of the delivery device shown in FIG. 1;

DETAILED DESCRIPTION

Figure 1:
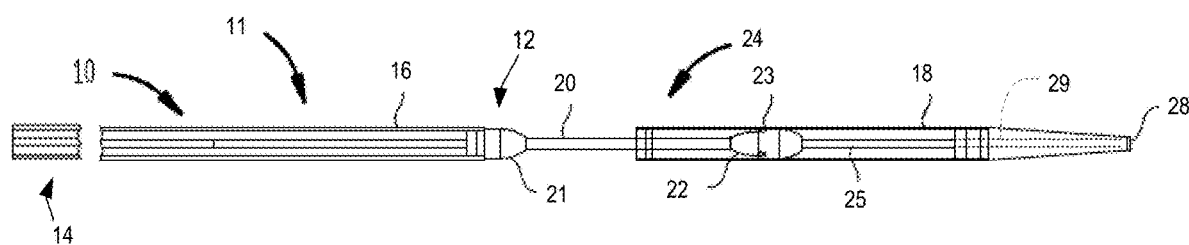
FIG. 1 is a side view of a distal portion of a delivery device.

Embodiments of the presently disclosed delivery devices are described herein in detail with reference to the drawing figures, wherein like reference numerals identify similar or identical elements. In the drawings and in the description which follows, the term "proximal" refers to the end of a delivery device, or portion thereof, which is closest to the operator in use, while the term "distal" refers to the end of the delivery device, or portion thereof, which is farthest from the operator in use when the delivery device is inserted into a patient. Also as used herein, the terms "about," "generally" and "approximately" are intended to mean that slight deviations from absolute are included within the scope of the term so modified.

Figure 2:
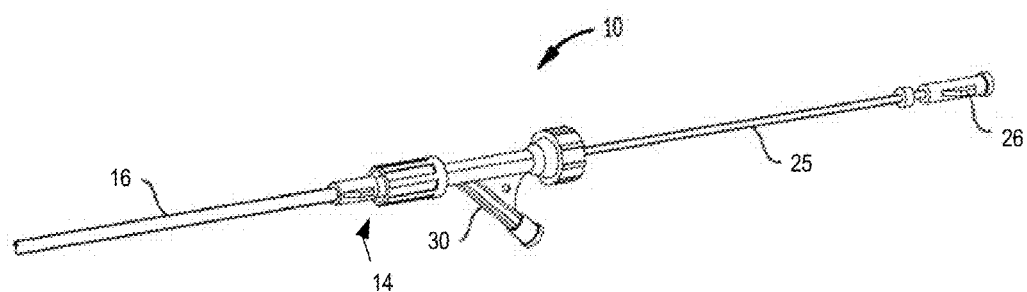
FIG. 2 is a perspective view of a proximal portion of the delivery device of FIG. 1.

As seen in FIGS. 1 and 2, delivery device 10 used in one embodiment of the disclosure includes catheter assembly 11 having first end 12 and second end 14. Catheter assembly 11 has outer shaft 16 extending between the first and second ends, distal sheath 18 and inner shaft 20 extending therebetween. Proximal retainer 21 is fixed to first end 12 of catheter assembly 11. Hollow inner shaft 20 is fixed to the proximal retainer and projects distally therefrom. Distal retainer 22 and retaining element 23 are mounted to inner shaft 20 remote from proximal retainer 21, so that distal retainer 22 and retaining element 23 are disposed distal to proximal retainer 21. Retainers 21 and 22 thus define valve receiving compartment 24 between them. For delivery into a patient, a collapsible valve is loaded into valve receiving compartment 24 around inner shaft 20 and between retainers 21 and 22, and a stent portion of the valve is coupled to retaining element 23. When the valve is loaded in compartment 24 and distal sheath 18 is in a fully closed position, the distal sheath encloses the compartment and maintains the valve in a collapsed condition.

Hollow inner tube 25 has hub 26 (FIG. 2) at its proximal end, atraumatic tip 28 (FIG. 1) at its distal end, and a lumen extending from the hub to the tip. The lumen of inner tube 25 communicates with bore 29 in tip 28. In use, a guidewire can be inserted into bore 29 and through the lumen of inner tube 25 as delivery device 10 is guided to a target site in the patient. Distal sheath 18 may be connected to tip 28 and extend proximally from the tip. Distal sheath 18 has substantially the same diameter as outer shaft 16. Inner tube 25 is slidably received within catheter assembly 11 and inner shaft 20. Thus, inner tube 25, atraumatic tip 28 and distal sheath 18 can be moved proximally and distally relative to catheter assembly 11 and retainers 21 and 22, between a fully closed position in which distal sheath 18 entirely covers compartment 24 and the retainers, and a fully open position in which the compartment is uncovered and the proximal end of distal sheath 18 is distal to retainer 22.

Hub 26 is adapted for connection to another system or mechanism, such as an operating handle (not shown) for displacing inner tube 25 and distal sheath 18 relative to catheter 11 and retainers 21 and 22. Mechanisms for displacing distal sheath 18 between its proximal and distal positions are described in International Patent Application Publication No. WO/2009/091509, the disclosure of which is hereby incorporated herein by reference herein.

A fitting such as Y connector 30 may also be connected at second end 14 of outer shaft 16, and may include a hemostasis valve for hindering blood flow out from between inner tube 25 and outer shaft 16. Y connector 30 may also be coupled to a fluid source for flushing outer shaft 16 and for injecting fluids such as contrast media during a prosthetic valve implantation procedure.

Referring now to FIG. 3, retaining element 23 includes outer piece 40 and support piece 42 located adjacent to outer piece 40. Outer piece 40 includes one or more recesses 44 located at a retention edge 46 of the outer piece 40 and sized and shaped to receive a corresponding retention member of a stent of a collapsible prosthetic valve. Details of a collapsible prosthetic valve will be described in greater detail below with reference to FIG. 4A. That is each recess 44 preferably has a similar shape and a slightly larger size than retention members so as to capture same readily, but with only a small amount of relief therebetween. Recesses 44 are spaced apart from one another around the circumference of retaining element 23 and serve to maintain the prosthetic heart valve in assembled relationship with delivery device 10, to minimize longitudinal movement of the prosthetic heart valve relative to the delivery device during unsheathing and resheathing procedures, to help prevent rotation of the prosthetic heart valve relative to the delivery device as the delivery device is advanced to the target site and during deployment, and to maintain the alignment of stent cells and prevent them from becoming tangled.

Figure 4A:
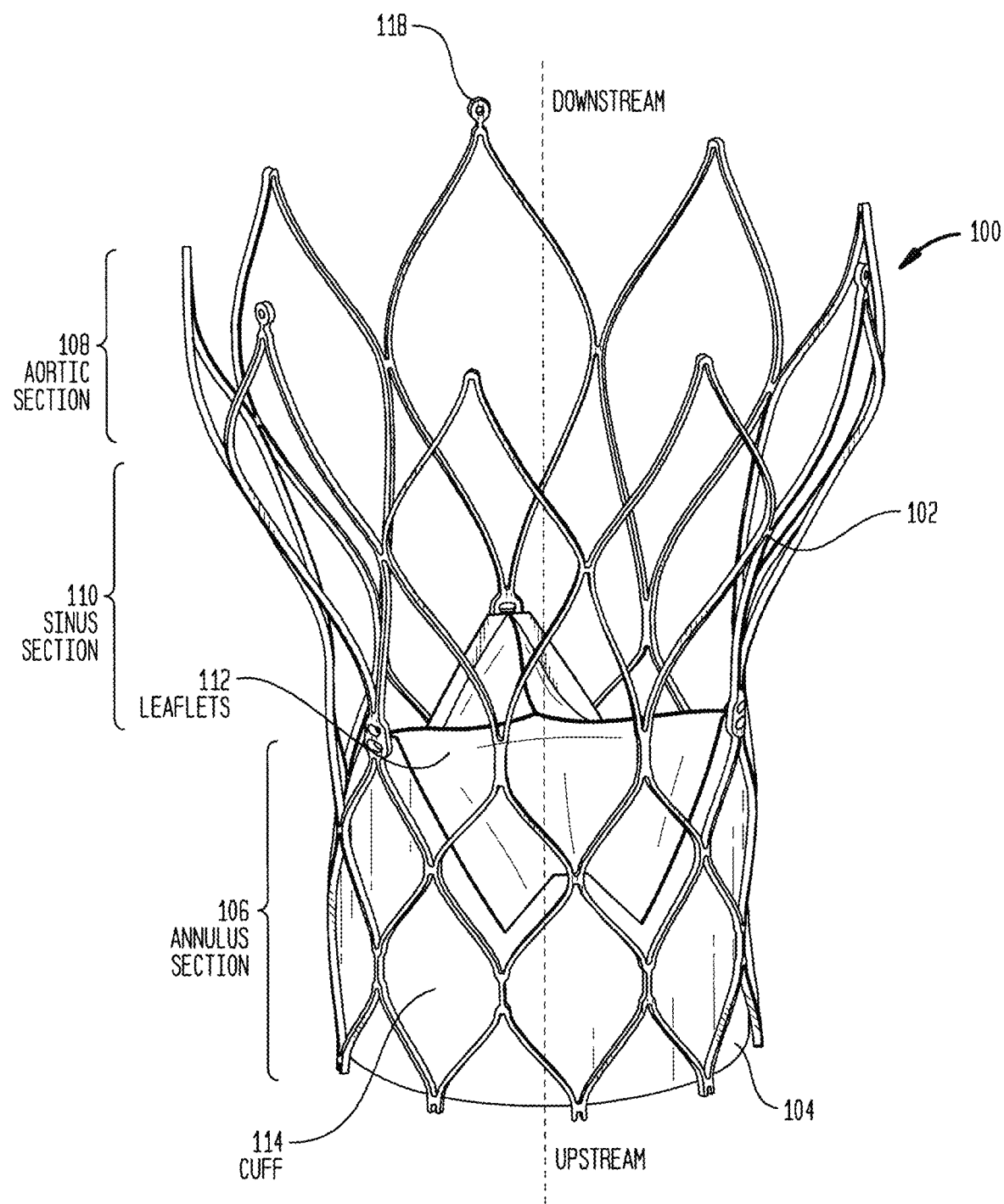
FIG. 4A is a perspective view of a self-expanding prosthetic heart valve.

Delivery device 10 may be used to implant a prosthetic heart valve designed to replace a native aortic valve. FIG. 4A shows an example of one such device, bioprosthetic valve 100, which has a collapsed condition and an expanded condition. Valve 100 may be formed from a collapsible framework or stent 102, with a valve assembly 104 internally connected to the stent. The stent 102 may be formed from any suitable biocompatible material, such as nitinol or any other suitable elastic or shape memory material, and may include an annulus section 106, an aortic section 108, and a sinus section 110 located between the annulus section and the aortic section. The aortic section 108 may have a larger cross section than the annulus section 106. The valve assembly 104 includes a plurality of leaflets 112 and a cuff 114 attached to the stent 102. The leaflets 112 and the cuff 114 may be formed from a biocompatible polymer, from natural tissue such as bovine or porcine pericardial tissue, or from other appropriate biocompatible materials. The valve assembly 104 is preferably connected to the stent 102 generally within the annulus section 106. The valve 100 may include a plurality of tabs or retainers 118 at spaced positions around one or both ends of the stent 102 for engagement with the retaining element 23 of the delivery device 10 as described above. The retainers 118 may also be utilized to collapse the valve 100 for loading into the delivery device 10, as will be discussed below.

The valve 100 is preferably stored in its expanded or open condition as the bioprosthetic valve assembly 104 may be compromised by storage in a collapsed condition for extended periods of time. As such, it is necessary to crimp the valve 100 into a collapsed condition of reduced cross-section for loading into the delivery device 10 just prior to the surgical implantation procedure. In order to effectively limit the time period the valve 100 is collapsed, the crimping process is preferably conducted in the operating arena by the surgeon, interventional cardiologist or surgical assistant using a specialized assembly.

Figure 4B:
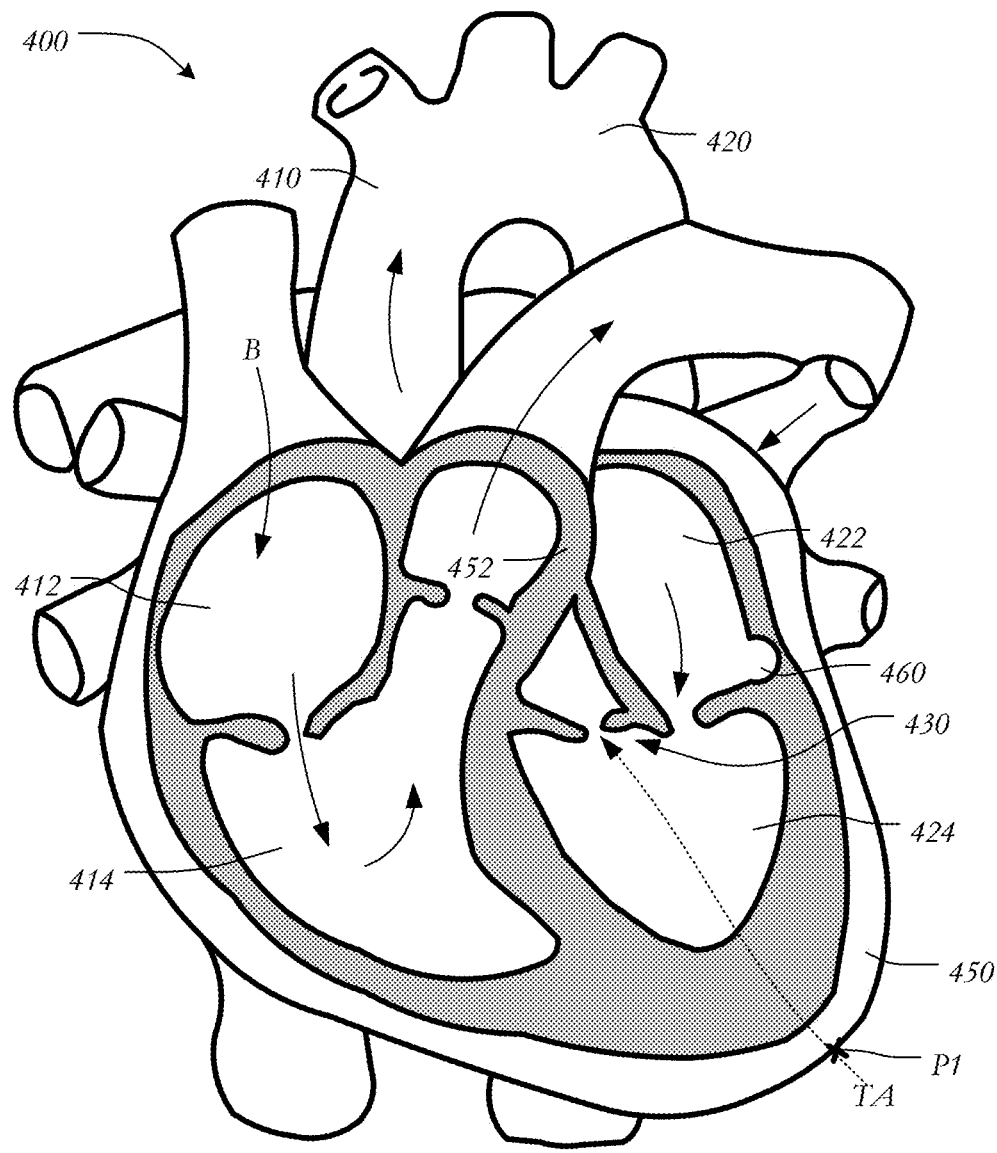
FIG. 4B is a schematic representation of a human heart showing a transapical delivery approach.

FIG. 4B is a schematic representation of a human heart 400. The human heart includes two atria and two ventricles: a right atrium 412 and a left atrium 422, and a right ventricle 414 and a left ventricle 424. As illustrated in FIG. 4B, the heart 400 further includes an aorta 410, and an aortic arch 420. Disposed between left ventricle 424 and aorta 410 is aortic valve 430. During ventricular systole, pressure rises in left ventricle 424. When the pressure in the left ventricle rises above the pressure in aorta 410, aortic valve 430 opens, allowing blood to exit left ventricle 424 into the aorta 410. When ventricular systole ends, pressure in left ventricle 424 rapidly drops. When the pressure in left ventricle 424 decreases, the aortic pressure forces aortic valve 430 to close. Blood flows through heart 400 in the direction shown by arrows "B".

A dashed arrow, labeled "TA", indicates a transapical approach for treating or replacing heart tissue. In transapical delivery, a small incision is made between the ribs and into the apex of the left ventricle 424 at position "P1" in heart wall 450 to deliver the prosthetic heart valve to the target site. In order to more easily advance a catheter between the patient's ribs, through the apex of left ventricle 424 and to the target site, a catheter with greater flexibility than conventional catheters may preferably be employed.

Figure 5A:
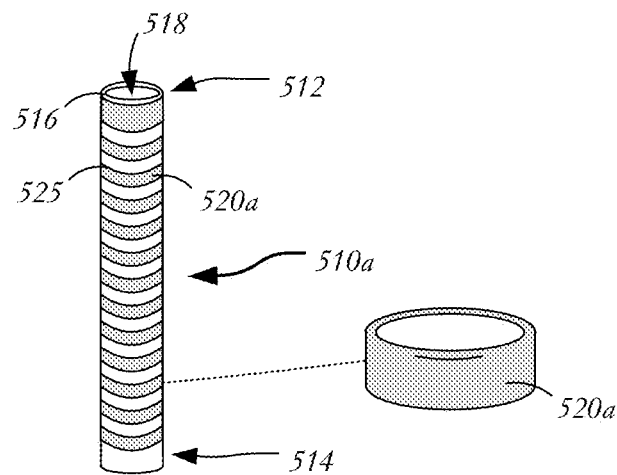
FIG. 5A is a perspective partial view of a segmented outer shaft according to the present disclosure.

In order to increase the flexibility of the delivery system, outer shaft 16 of delivery device 10 may be laser cut to form a series of disks. As shown in FIG. 5A, outer shaft 510a is formed of a generally cylindrical hypotube having first end 512 and second end 514. Outer shaft 510a may have a size of approximately 24 French or less and may include outer wall 516 defining lumen 518 extending therethrough from first end 512 to second end 514. Outer shaft 510a may be segmented into discrete disks 520a by making circumferential cuts at spaced distances along the length of the outer shaft by, for example, laser cutting. As FIG. 5A illustrates, if a straight line is cut around the circumference of outer shaft 510a, discrete and separable disks 520a are formed.

Figure 5B:
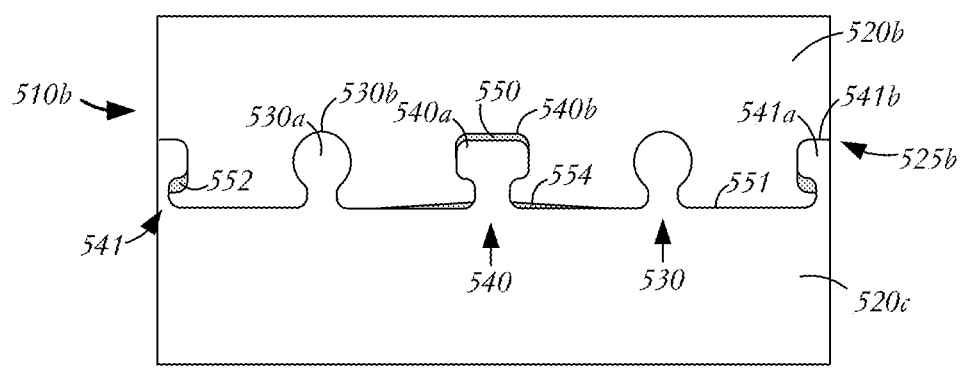
FIG. 5B is a schematic developed view of a first laser cutting pattern formed between two adjacent disks.

Instead of cutting a straight line, a pattern may be cut around the circumference of an outer shaft in order to provide discrete disks that are coupled to one another to increase flexibility. FIG. 5B is a developed view of outer shaft 510b showing the pattern 525b cut around the entire circumference of the outer shaft to form disks 520b, 520c.

Pattern 525b includes a generally circumferential straight cut line 551 (e.g., ring-shaped), interrupted by a series of hinges 530 that alternate with ribs 540 and 541. Each hinge 530 includes male hinge member 530a formed on first disk 520c and female hinge member 530b formed in adjacent second disk 520b. Male hinge members 530a have a generally circular head that is joined to first disk 520c by a narrowed neck. Female hinge members 530b have a complementary shape (e.g., a generally circular opening that is spaced from cut line 551 by a narrowed neck). Each disk, such as first disk 520c, may include two male hinge members 530a spaced apart by 180 degrees around the circumference of the outer shaft (e.g., male hinge members 530a may be on directly opposite sides of the outer shaft).

Rib 540 includes male rib member 540a formed in first disk 520c and female rib member 540b formed in second disk 520b. Male rib member 540a has a generally rectangular head that is joined to first disk 520c by a narrowed neck. Female rib member 540b has a substantially complementary shape—a generally rectangular opening that is spaced from cut line 551 by a narrowed neck. However, the rectangular opening in female rib member 540b is larger than the rectangular head of male rib member 540a so that a first open area 550, is formed at the free end of rib member 540a. Additionally, material may be removed from second disk 520b along cut line 551 on either side of female rib member 540b so as to form triangular cutouts 554 between disks 520b and 520c. The purpose of open areas 550 and triangular cutouts 554 will become apparent from the description below. Preferably, rib 540 is positioned about halfway between hinges 530, i.e., about 90 degrees from each hinge. Second rib 541 is substantially the same as first rib 540, and includes a male rib member 541a formed on first disk 520c and a female rib member 541b formed in second disk 520b. The primary differences between second rib 541 and first rib 540 is that female rib member 541b is enlarged relative to male rib member 541a so as to form second open areas 552 closer to cut line 551 on either side of the narrowed neck of male rib member 541a, and second rib 541 does not include triangular cutouts 554. Second rib 541 preferably is positioned about halfway between hinges 530, i.e., about 90 degrees from each hinge and about 180 degrees from first rib 540. Cutting pattern 525b thus forms in outer shaft 510b two adjacent disks 520b, 520c that are coupled together yet able to articulate relative to one another. An amount of articulation of between 0 and about 10 degrees is possible between adjacent disks. In at least some examples, the maximum articulation between adjacent disks may be between about 2 degrees and about 8 degrees, or between about 4 degrees and about 6 degrees (e.g., the maximum articulation may be about 5 degrees). Ribs 540, 541 provide lateral strength such that disks 520b, 520c do not detach from one another, and provide strength against transverse bending loads as will be described with reference to FIG. 5D. Similar patterns may be cut around the circumference of outer shaft 510b at spaced intervals along the length of the outer shaft to form a segmented outer shaft having a plurality of disks.

Figure 5C:
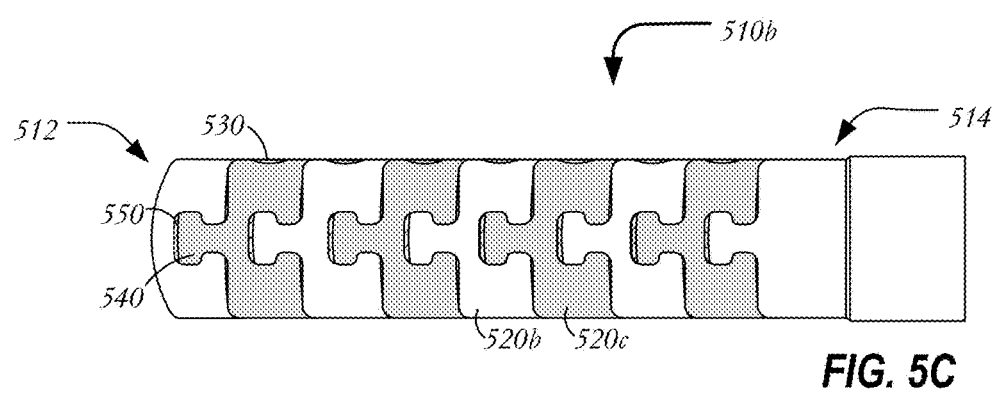
FIG. 5C is a side view of a segmented outer shaft after laser cutting.
Figure 5D:
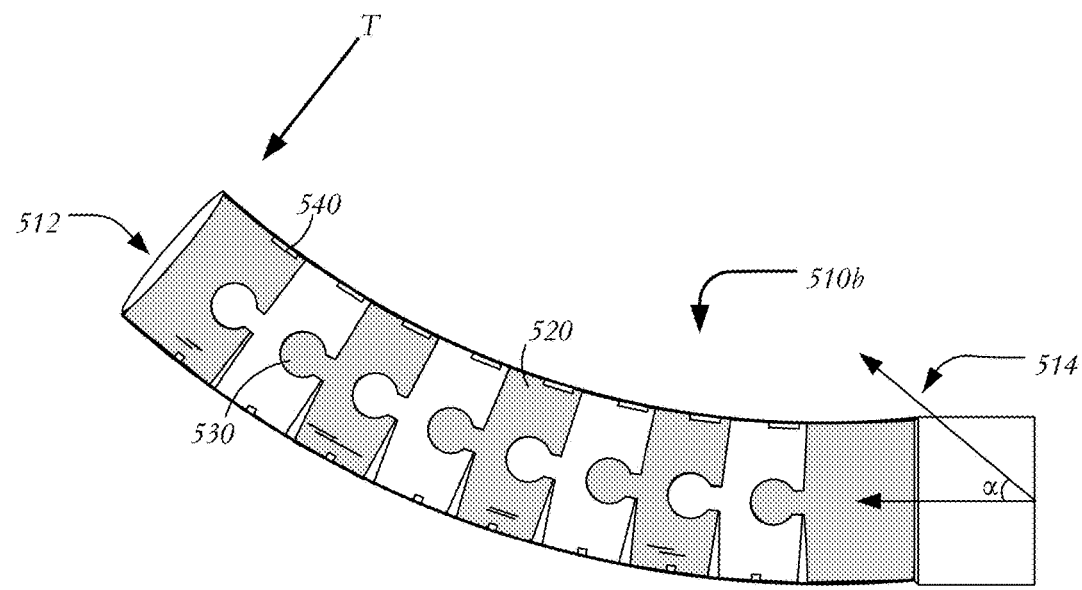
FIG. 5D is a perspective view of the bending of an outer shaft after laser cutting.

FIG. 5C illustrates segmented outer shaft 510b, which has been repeatedly laser cut according to the pattern 525b shown in FIG. 5B to form disks 520b and 520c having hinges 530, and ribs 540 and 541 (not shown). Having laser cut outer shaft 510b to form discrete disks 520b and 520c, each disk is able to articulate relative to an adjacent disk as shown in FIG. 5D. The total result of forming multiple disks along the length of outer shaft 510b is an outer shaft capable of unidirectional bending to a bending angle α with respect to the central axis at the second end 514 of outer shaft 510b. In this example, motion is limited to unidirectional bending because of the configuration of the open areas—namely that first open area 550 is only disposed above first rib 540 (e.g., between head of male 540a and female 540b) while second open areas 552 are disposed below second rib 541 (e.g., on either side of the narrowed neck of male rib member 541a). Additionally, if a load, such as transverse bending load "T" shown in FIG. 5D is applied to outer shaft 510b, ribs 540 are capable of providing strength against this load, portions of ribs 540 being capable of bearing at least some of the stress from bending load "T".

In some examples, the bending angle α may be between about 0 degrees (e.g., in a straight line parallel to the central axis) and about 60 degrees. In at least some examples, the bending angle α may be between about 0 degrees and about 40 degrees. In some examples, bending angle α may be between about 30 degrees and about 50 degrees (e.g., bending angle α may be about 45 degrees). Moreover, after forming disks 520b and 520c as desired, a polymer jacket may be applied around the outer shaft to provide an atraumatic outer surface as outer shaft traverses the patient's vasculature. A polymer jacket may also be capable of providing a predetermined amount of stiffness so that there is a small returning force to maintain the catheter in a straight configuration absent external forces. For longer, multi-directional shafts this stiffness may provide a level of "pushability" so that the catheter does not snake up when it encounters a push back load during tracking.

Thus, as a result of a structural backbone being formed largely of a tubing material and not a reinforced polymer and other features of this construction, a catheter formed in this manner is capable of providing a higher compression resistance and torqueability at the diameters described (e.g., approximately 24 French) when compared to traditional braided shaft constructions. Additionally, catheters formed as described are extremely flexible while maintaining the desired compression resistance and torqueability, without relying on bending or flexural members within outer shaft 510b or resorting to more expensive materials, such as nitinol. Additionally, the described configurations provide the necessary flexion without requiring strain members.

Though two hinges 530 and two ribs 540 and 541 are shown on each disk 520, it will be understood that more or fewer of the hinges and/or ribs are possible. Additionally, the number of hinges and ribs may be the same or be different, with more hinges provided than ribs, or vice versa. The number of disks 520b and 520c may also vary as desired, with a greater number of disks providing greater flexibility and a lesser number of disks providing less flexibility. In some examples, as few as two hinges and one rib are provided. Moreover, while the pattern above has been described as being laser cut, it will be understood that other methods of cutting outer shaft 510b are possible including, but not limited to water jet cutting, plasma cutting, chemical etching, conventional machining and/or electrical discharge machining.

Figure 6A:
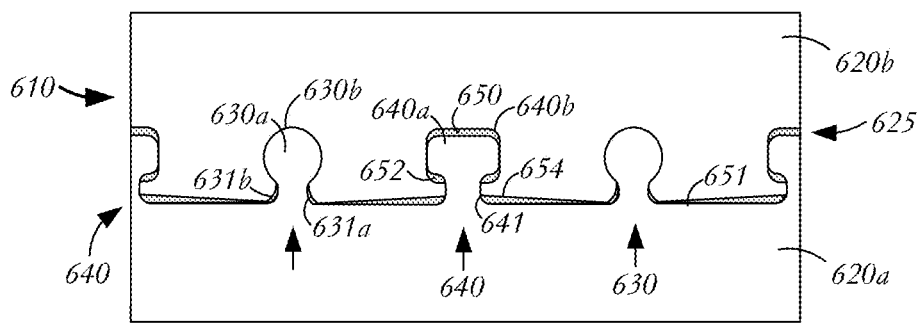
FIG. 6A is a schematic developed view of a second laser cutting pattern formed between two adjacent disks.
Figure 6B:
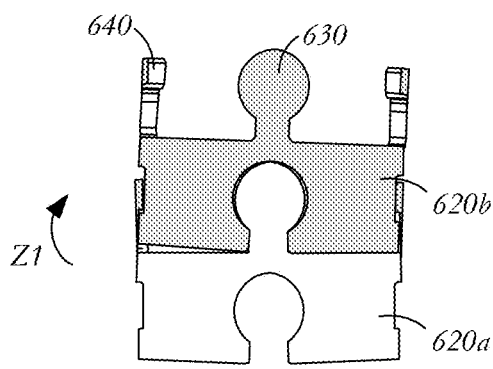
FIGS. 6B and 6C are schematic representations of the bending of two disks after providing the second laser cutting pattern.
Figure 6C:
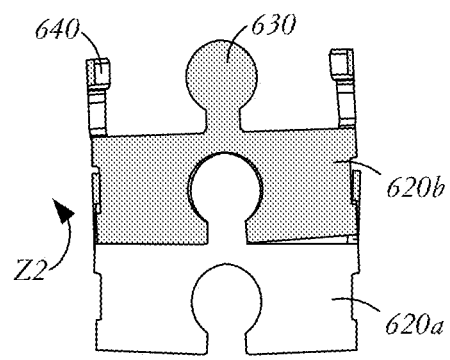

In a variation of the embodiment described above, the cutting pattern may be modified to enable bending in more than a single direction. An outer shaft 610 capable of bidirectional bending will be described with reference to FIG. 6A. FIG. 6A is a developed view of outer shaft 610 showing the pattern 625 cut around the active circumference of the outer shaft to form disks 620a, 620b. Similar to pattern 525, pattern 625 includes two hinges 630 that alternate with two ribs 640 around the circumference of outer shaft 610. Hinges 630 include male hinge members 630a on first disk 630a and female hinge members 630b formed in second disk 620b. Hinges 630 differ from hinges 530 described above in that the neck 631b of female hinge members 630b are slightly enlarged relative to neck 631a of male hinge members 630a to form a gap therebetween. Ribs 640 include male rib member 640a formed in first disk 620a and female rib member 640b formed in second disk 620b. Male rib member 640a has a generally rectangular head that is joined to disk 620a by narrowed neck 641. Female rib member 640b has a substantially complementary shape—a generally rectangular opening that is spaced from cut line 651 by a narrowed neck. However, the rectangular opening in female rib member 640b is larger than the rectangular head in male rib member 640a so that an open area 650, is formed at the free end of rib member 640a between the generally rectangular head of male rib member 640a and female rib member 640b. Female rib member 640b is also enlarged and slightly elongated relative to male rib member 640a so as to form open areas 652 closer to cut line 651 on either side of the narrowed neck of male rib member 640a. Thus, each rib 640 includes both open areas 650 and 652 as opposed to ribs of the previous embodiment where each rib includes only one of the open areas 550,552. Additionally, material may be removed from second disk 620b along cut line 651 on either side of female rib member 640b so as to form triangular cutouts 654 between disks 620a and 620b. This specific configuration of open areas 650,652 on each rib 640 permits disks 620a,620b to articulate relative to one another in two directions. That is, second disk 620b is capable of articulating in a first direction Z1 (FIG. 6B) with respect to first disk 620a, as well as in a second opposite direction Z2 (FIG. 6C) due to the presence of cutouts 654, and open areas 650,652 on each rib 640, which allows male rib member 640a and female rib member 640b of each rib 640 to be displaced relative to one another in two directions.

Figure 7A:
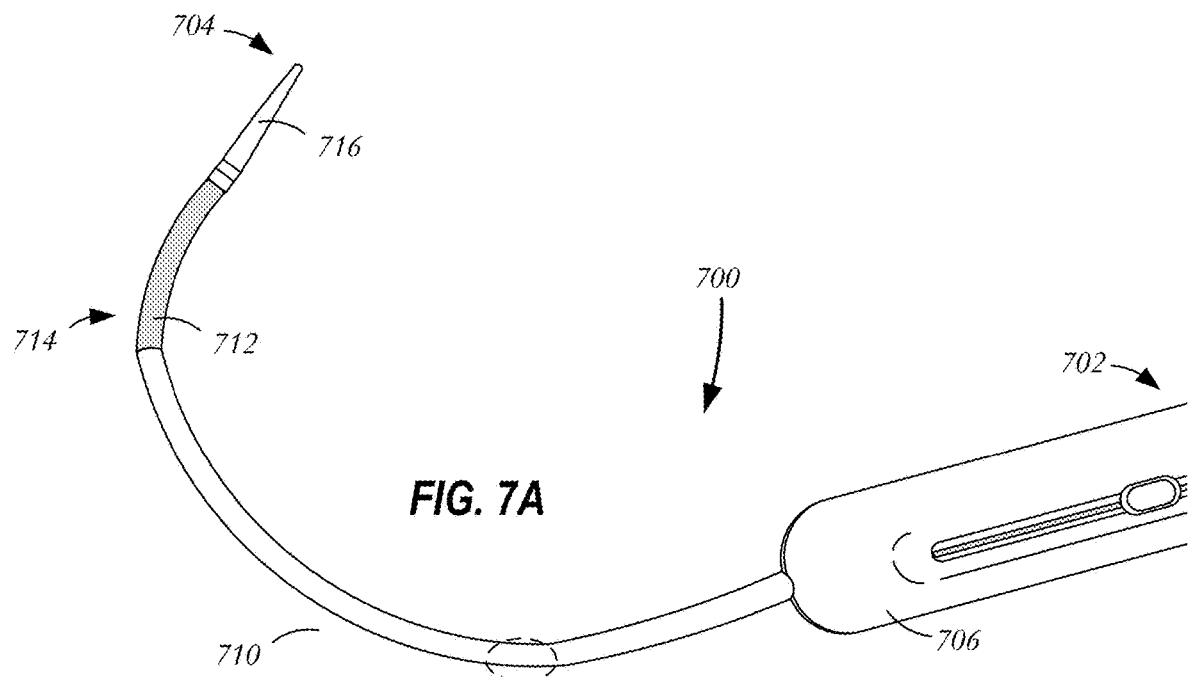
FIG. 7A is a schematic perspective view of the bending of an outer shaft.
Figure 7B:
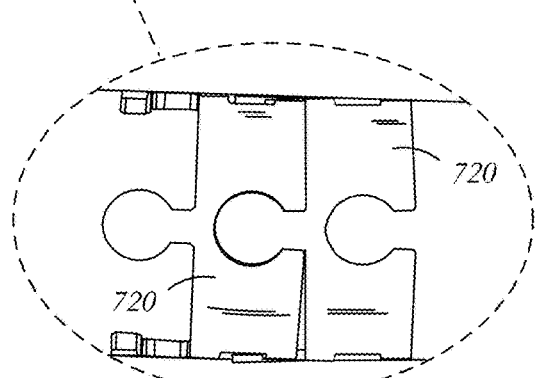
FIG. 7B is an enlarged partial view of the bending of two disks forming a portion of the outer shaft of FIG. 7A.

FIGS. 7A and 7B illustrate the use of delivery device 700 having features of the present disclosure to implant a medical device, such as a prosthetic heart valve. Delivery device 700 may include all of the features discussed above with reference to FIGS. 1-3 and generally includes proximal end 702 and distal end 704. Delivery device 700 includes operating handle 706 for use by a physician or operator coupled at one side to outer shaft 710. Outer shaft 710 extends to slidable distal sheath 712 covering compartment 714 for housing a prosthetic heart valve (not shown) disposed about an inner shaft (also not shown). The delivery device 700 further includes a conical atraumatic tip 716 at distal end 704. As shown in the enlargement of FIG. 7B, the outer shaft 710 includes disks 720 that articulate relative to one another to enable the outer shaft to more readily bend or flex during use, making the implantation process easier and quicker.

Figure 8A:
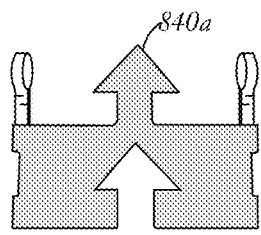
FIGS. 8A-C are schematic representations of several variations for forming ribs on disks.
Figure 8B:
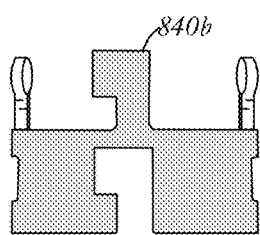
Figure 8C:
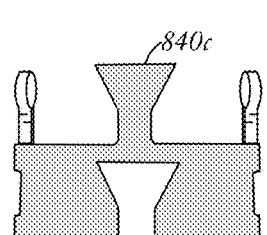

It will be understood that several variations of the above disclosure are possible. For example, though the ribs have been described as being substantially rectangular with a narrowed neck, other shapes are possible. The ribs may be arrow-shaped as shown at 840a in FIG. 8A, L-shaped as shown at 840b in FIG. 8B, or trapezoidal shaped as shown at 840c in FIG. 8C. Thus, the shape, the number and/or the size of the ribs may be varied as desired.

Figure 9:
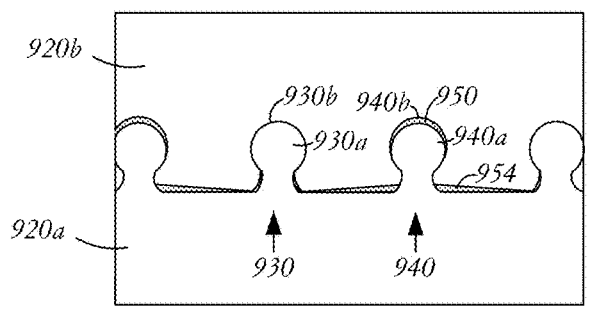
FIG. 9 is a schematic representation of disks having circular ribs.

Additionally, though the ribs and the hinges have been shown as being shaped differently from one another, it will be understood that the ribs and hinges may also be cut into the same shape. For example, FIG. 9 is a schematic illustration showing disks 920a,920b having substantially circular hinges 930 including male hinge members 930a and female hinge members 930b, and substantially circular ribs 940 including male rib members 940b and female rib members 940a. Triangular cutouts 954 are provided adjacent each rib 940 similar to cutouts 654 of FIG. 6A. The inclusion of open areas 950 above ribs 940 and cutouts 954 may allow the proper articulation of disks 920a, 920b with respect to one another.

Figure 10:
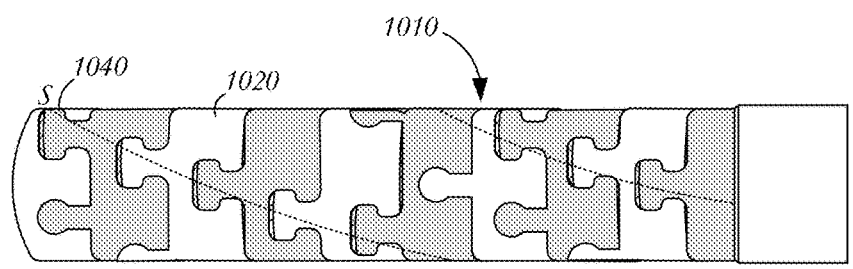
FIG. 10 is a schematic representation of another variation of laser cutting having spirally aligned laser cutting patterns.

FIG. 10 is another variation of the outer shaft according to the present disclosure. In this example, outer shaft 1010 includes a plurality of disks 1020 that have been laser cut in a pattern similar to that described above with reference to FIG. 6A. However, rather than having the hinges and ribs aligned axially with one another as shown in FIG. 5C adjacent disks 1020 in this variant have been cut so that the hinges and ribs are not axially aligned. Instead, the male hinge and rib members on each disk are offset circumferentially from the female hinge and rib numbers on that disk so that the hinges and ribs form a spiral pattern "S" along the length of outer shaft 1010. This pattern may be appreciated by examining the positions of ribs 1040 in adjacent disks 1020. In this instance, the ribs 1040 on each disk 1020 are offset from the ribs on an adjacent disk by predetermined amount, ranging from about 0 degrees and about 60 degrees (e.g., offset by 30 degrees, 45 degrees of 60 degrees). By forming circumferential patterns that are offset from one another by other than 180 degrees, outer shaft 1010 may be capable of freely articulating in multiple directions, with smaller circumferential offsets resulting in a great number of directions of articulation.

It is to be understood that numerous modifications may be made to the illustrative embodiments and that other arrangements may be devised without departing from the spirit and scope of the present disclosure as defined by the appended claims. For example, though the delivery system has been shown as a transapical delivery system, it will be understood that the teachings of the present disclosure are not so limited and that similar cutting patterns and disks may be formed on transfemoral, transseptal or other delivery systems. Additionally, while the examples have been shown for a delivery system for transcatheter aortic valve replacement, the disclosed teachings are equally applicable for other valve replacement, such as for example, mitral valve replacement, as well as other catheters for valve replacement and/or repair. Moreover, the present disclosure may also be applied to catheters for other medical purposes, such as the implantation of stents and other medical devices, other types of percutaneous or laparoscopic surgical procedures and the like.

In some embodiments, a delivery device for a collapsible prosthetic heart valve includes an outer shaft having a first end and a second end, an inner shaft disposed inside the outer shaft and longitudinally movable relative to the outer shaft, and a distal sheath coupled to the inner shaft and movable with the inner shaft to selectively cover and uncover a compartment for housing the valve. The outer shaft includes a plurality of disks each having at least two hinges to allow articulation of adjacent disks relative to one another, and at least one rib for coupling the adjacent disks to one another.

In some examples, the at least one rib may have a generally rectangular head, and/or the at least one hinge may have a substantially circular head, and/or each disk may include two hinges disposed on opposite sides of the disk, and/or each disk may include two ribs circumferentially arranged about the disk, and/or the at least one hinge of each disk may be axially aligned with other hinges of adjacent disks, and/or the at least one hinge of each disk may be circumferentially offset from the at least one hinge of adjacent disks by a predetermined amount, and/or the predetermined amount may be between about 0 degrees and about 60 degrees, and/or each disk may be capable of a maximum articulation of between about 2 degrees and about 8 degrees relative to an adjacent disk, and/or adjacent disks may be capable of articulating relative to one another such that the outer shaft is capable of a maximum bending angle of between about 30 degrees and about 50 degrees with respect to a central axis of the second end of the outer shaft, and/or the outer shaft may be capable of articulating in one direction relative to a central axis at the second end the outer shaft, and/or the outer shaft may be capable of articulating in multiple directions relative to a central axis at the second end the outer shaft, and/or each of the plurality of disks may include an equal number of ribs and hinges, and/or the device may further include a polymeric jacket disposed on an outer surface of the outer shaft.

In some embodiments, a catheter includes an elongated tubular body having a first end and a second end and including a plurality of disks each having at least two hinges to allow articulation of adjacent disks relative to one another, and at least one rib for coupling the adjacent disks to one another.

In some embodiments, a method of forming a delivery device for a collapsible prosthetic heart valve includes providing an outer shaft having a first end and a second end, an inner shaft disposed inside the outer shaft and longitudinally movable relative to the outer shaft, and a distal sheath coupled to the inner shaft and movable with the inner shaft to selectively cover and uncover a compartment for housing the valve. A series of circumferential patterns may be cut on the outer shaft at different axial lengths to form a plurality of disks each having at least two hinges to allow articulation of adjacent disks relative to one another, and at least one rib for coupling the adjacent disks to one another.

In some examples, the cutting step may include cutting alternating hinges and ribs on each of the plurality of disks around the circumference of each disk, and/or the method may further include coupling a polymeric jacket to the outer shaft after cutting the outer shaft, and/or the cutting step may include cutting a pattern on each of the plurality of disks, the pattern on each of the plurality of disks being offset in a circumferential direction from the pattern on an adjacent disk, and/or the cutting step may include using a laser to cut the outer shaft.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A delivery device for a collapsible prosthetic heart valve, the delivery device comprising:
   an outer shaft having a first end and a second end, the outer shaft including a plurality of disks, each disk having an outer surface extending in a circumferential direction, adjacent disks defining at least one hinge to allow articulation of the adjacent disks relative to one another and at least one rib adjacent to the at least one hinge for coupling the adjacent disks to one another, the at least one hinge including male hinge member extending from a first one of the adjacent disks and female hinge member formed in a second one of the adjacent disks, the at least one rib including male rib member extending from the first one of the adjacent disks and female rib member formed in the second one of the adjacent disks;
   an inner shaft disposed inside of the outer shaft and longitudinally movable relative to the outer shaft; and
   a distal sheath coupled to the inner shaft and movable with the inner shaft to selectively cover and uncover a compartment for housing the valve,
   wherein the female hinge member defines a neck receiving portion in the second one of the adjacent disks and a substantially circular head receiving portion in communication with the neck receiving portion of the female hinge member, and the female rib member defines a neck receiving portion in the second one of the adjacent disks and a generally rectangular head receiving portion in communication with the neck receiving portion of the female rib member, a width of the generally rectangular head receiving portion in the circumferential direction being greater than a width of the neck receiving portion of the female rib member in the circumferential direction, and the second one of the adjacent disks being tapered such that a cutout is formed between the first one of the adjacent disks and the second one of the adjacent disks, the cutout extending in the circumferential direction from the neck receiving portion of the female rib member and terminating at a position intermediate the neck receiving portion of the female rib member and the neck receiving portion of the adjacent female hinge member such that each disk is capable of a maximum articulation of between about 2 degrees and about 8 degrees relative to an adjacent disk.

2. The delivery device of claim 1, wherein each disk has two female hinge members, one of the female hinge members is disposed on a first side of the disk and the other one of the female hinge members is disposed on a second side of the disk opposite the first side.

3. The delivery device of claim 1, wherein each disk has two female rib members circumferentially arranged about the disk.

4. The delivery device of claim 3, wherein a first one of the two female rib members and a first corresponding male rib member define an empty space between a closed end of the head receiving portion of the first female rib member and the first corresponding male rib member and a second one of the two female rib members and a second corresponding male rib member define an empty space between an open end of the head receiving portion of the second female rib member and the second corresponding male member.

5. The delivery device of claim 1, wherein the at least one female hinge member of each disk is axially aligned with the at least one female hinge members of adjacent disks.

6. The delivery device of claim 1, wherein the at least one female hinge member of each disk is circumferentially offset from the at least one female hinge member of adjacent disks by a predetermined amount.

7. The delivery device of claim 6, wherein the predetermined amount is between about 0 degrees and about 60 degrees.

8. The delivery device of claim 1, wherein adjacent disks are capable of articulating relative to one another such that the outer shaft is capable of a maximum bending angle of between about 30 degrees and about 50 degrees with respect to a central axis of the second end of the outer shaft.

9. The delivery device of claim 1, wherein the outer shaft is capable of articulating in one direction relative to a central axis of the second end of the outer shaft.

10. The delivery device of claim 1, wherein the outer shaft is capable of articulating in multiple directions relative to a central axis at the second end of the outer shaft.

11. The delivery device of claim 1, wherein each of the plurality of disks has an equal number of female rib members and female hinge members.

12. The delivery device of claim 1, further comprising:
a polymeric jacket disposed on an outer surface of the outer shaft.

13. A catheter comprising:
an elongated tubular body having a first end and a second end and including a plurality of disks, each disk having an outer surface extending in a circumferential direction, adjacent disks defining at least two hinges to allow articulation of the adjacent disks relative to one another and at least two ribs for coupling the adjacent disks to one another, each one of the hinges including a male hinge member extending from a first one of the adjacent disks and a female hinge member formed in a second one of the adjacent disks, each one of the ribs including a male rib member extending from the first one of the adjacent disks and a female rib member formed in the second one of the adjacent disks, wherein the female hinge member has a neck receiving portion in the second one of the adjacent disks and a substantially circular head receiving portion in communication with the neck receiving portion of the female hinge member and the female rib member includes a neck receiving portion in the second one of the adjacent disks and a generally rectangular head receiving portion in communication with the neck receiving portion of the female rib member, a width of the generally rectangular head receiving portion in the circumferential direction being greater than a width of the neck receiving portion of the female rib member in the circumferential direction, and the second one of the adjacent disks being tapered such that a cutout is formed between the first one of the adjacent disks and the second one of the adjacent disks, the cutout extending in the circumferential direction from the neck receiving portion of a first one of the female rib members and terminating at a position intermediate the neck receiving portion of the first one of the female rib members and the neck receiving portion of an adjacent one of the female hinge members such that each disk is capable of a maximum articulation of between about 2 degrees and about 8 degrees relative to an adjacent disk.

* * * * *